US008798350B2

(12) United States Patent
Zou

(10) Patent No.: US 8,798,350 B2
(45) Date of Patent: Aug. 5, 2014

(54) METHOD AND SYSTEM FOR RECONSTRUCTION ALGORITHM IN CONE BEAM CT WITH DIFFERENTIATION IN ONE DIRECTION ON DETECTOR

(75) Inventor: Yu Zou, Naperville, IL (US)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 310 days.

(21) Appl. No.: 13/427,385

(22) Filed: Mar. 22, 2012

(65) Prior Publication Data

US 2013/0251224 A1 Sep. 26, 2013

(51) Int. Cl.
*G06K 9/00* (2006.01)
*A61B 6/00* (2006.01)
*G06T 11/00* (2006.01)

(52) U.S. Cl.
CPC ........... *G06T 11/006* (2013.01); *G06T 2211/40* (2013.01); *G06T 2211/421* (2013.01)
USPC ........................................... 382/131; 378/21

(58) Field of Classification Search
None
See application file for complete search history.

(56) References Cited

U.S. PATENT DOCUMENTS

| 6,973,157 | B2 * | 12/2005 | Claus ................................. 378/8 |
| 7,653,229 | B2 * | 1/2010 | Kaufhold et al. ............. 382/131 |
| 2012/0014582 | A1 * | 1/2012 | Schaefer et al. ............. 382/131 |

OTHER PUBLICATIONS

Zou, Yu, "Image Reconstruction on PI-lines by use of filtered back projection in helical cone-beam CT", Institute of Physics Publishing, Phys Med. Biol. 49 (2004), pp. 2717-2731.
Zou, Y., Pan, X., Sidky, E., "Theory and Algorithms for Image Reconstruction on Chords and within Regions of Interest", J. Opt Am. Soc., 22, 2005, pp. 2372-2384 (bearing Nos. 1-21).

* cited by examiner

*Primary Examiner* — Anand Bhatnagar
*Assistant Examiner* — Soo Park
(74) *Attorney, Agent, or Firm* — Yoshida & Associates, LLC

(57) ABSTRACT

The current invention is generally related to a data acquisition and or image processing method and system for acquiring and or processing sparse channel data. The sparse channel is implemented in a data acquisition system having a predetermined wider pitch between the adjacent detector cells than that in the currently available imaging systems at least in one predetermined direction. In one implementation, the sparse channel data is acquired by the sparse channel data acquisition system, and an image is reconstructed from the sparse channel data according to a predetermined chord based reconstruction method eliminating the differentiation along the channel direction and utilizing a pair of proper weights.

14 Claims, 7 Drawing Sheets

103A-1

103A-2

METHOD AND SYSTEM FOR RECONSTRUCTION ALGORITHM IN CONE BEAM CT WITH DIFFERENTIATION IN ONE DIRECTION ON DETECTOR

FIELD OF THE INVENTION

The current invention is generally related to image processing method and system for processing sparse channel data.

BACKGROUND OF THE INVENTION

Currently, commercially available computer tomography (CT) imaging systems are typically equipped with densely installed detector cells along predetermined directions. A detector cell means an individual sensor of a two-dimensional array of detectors or detector elements. The detector elements are adjacently installed on a predetermined surface. CT-scanners are geometrically as efficient as possible in closely placing a full complement of the detectors.

Due to the full complement of dense detector elements, currently available CT imaging systems are expensive. The high costs are substantially due to the above described a large number of detector cells along the channel directions. In addition, an equally large number of necessary electronics units associated with the detector cells also contributes to the expensive costs of these imaging systems. The high costs are even more critical using photon counting detectors rather than integrating detectors. In general, regardless of a detector type, the denser the detector cells are, the more expensive the imaging system becomes. In general, finely pitched detectors of the standard design dramatically increase the hardware costs.

Due to the densely packed integrating detector elements, currently available CT imaging systems also suffer from some undesirable cross-talk effects. Because of proximity of the adjacent detector elements, X-ray arriving at the detectors are scattered across and over the adjacent detector elements. The densely packed detector elements generally make the scattering correction difficult to achieve a desirable result in reconstructing an artifact-free image.

In this regard, most of currently practiced reconstruction methods in CT also assume the full complement of densely packed detector channels. These reconstruction methods include filtered backprojection, backprojection filtering and some forms of iterative reconstruction.

In view of the above discussed prior art issues, a practical solution is still desired for a method and a system for reconstructing an image without substantially affecting image quality based upon projection data that is acquired from detectors having a sparse direction so as to ultimately reduce the high costs of the detector elements and the associated electronics in the standard CT systems.

DETAILED DESCRIPTION OF THE PREFERRED EMBODIMENT(S)

Figure 1:
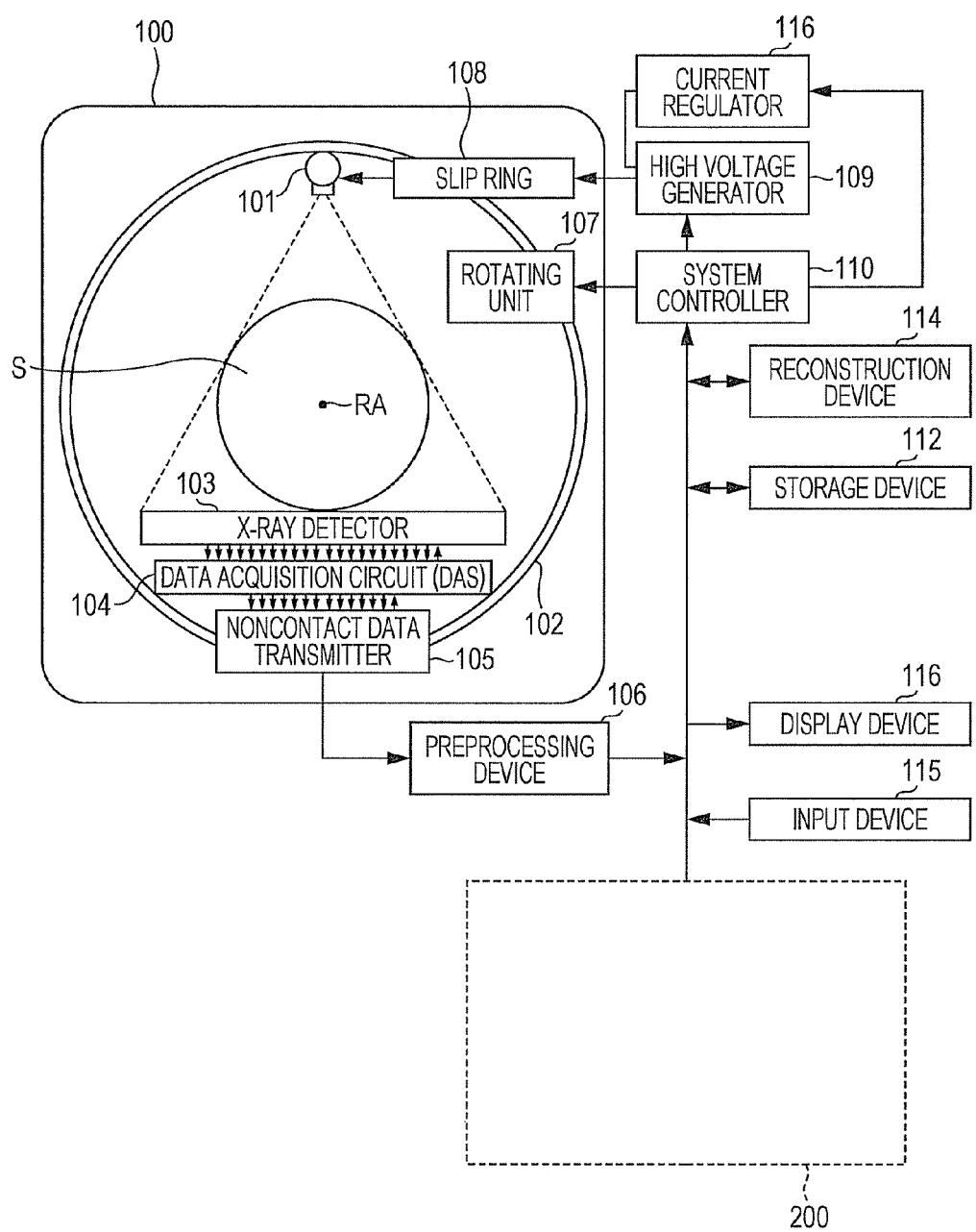
FIG. 1 is a diagram illustrating one embodiment of the multi-slice X-ray CT apparatus or scanner according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a front view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which rotates around axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that applies a tube voltage to the X-ray tube 101 so that the X-ray tube 101 generates X ray. In one embodiment, the high voltage generator 109 is mounted on the frame 102. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR).

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, display device 116, input device 115, and the scan plan support apparatus 200. The scan plan support apparatus 200 includes a function for supporting an imaging technician to develop a scan plan.

According to one aspect of the current invention, the X-ray detector 103 of the CT apparatus is advantageously configured to implement the detector sparse channels having a predetermined increased pitch between the detector cells or elements on a surface of the X-ray detector 103 in one embodiment. According to the current invention, the embodiment of the X-ray detector 103 has a certain predetermined range of a total number of the detector cells, and the predetermined range generally corresponds to a predetermined fractional range of a full complement of the currently available or conventional prior art X-ray detector cells.

One embodiment of the reconstruction device 114 includes various software and hardware components. According to another aspect of the current invention, the reconstruction device 114 of the CT apparatus advantageously eliminates certain derivatives along a certain detector direction along which projection data is sparsely sampled. Furthermore, the reconstruction device 114 of the CT apparatus advantageously determines proper weights for the projection data due to the certain detector direction along which projection data is sparsely sampled. The reconstruction device 114 subsequently backprojects a combination of the projection data and the derivation with the proper weights on to selected chords. The reconstruction device 114 ultimately obtains an image of desired quality despite the sparsity along a certain detector direction in the originally acquired projection data.

Assuming that the size of the detector cells remains in an embodiment according to the current invention, as a reduced number of the detector cells is placed on the same surface area of a detector unit, a wider pitch results between at least some pairs of the detector cells. In certain embodiments, the reduced number of the detector cells is installed on the detector unit surface at a predetermined equidistance from each other in one embodiment. Alternatively, the reduced number of the detector cells is installed on the detector unit surface at a predetermined non-uniform distance between the adjacent detector cells in another embodiment.

In the current application, the term, "sparse channel" or "detector sparse channel" is defined to generally encompass embodiments of the data acquisition system having a predetermined wider pitch between the adjacent detector cells or elements than that in the currently available imaging systems at least in one predetermined channel direction. The sparse channel is also defined to encompass various imaging modalities including CT, positron emission tomography (PET) and positron emission tomography-computed tomography (PET/CT). By the same token, the term, "sparse channel data" is defined to generally encompass data that is acquired by the embodiments of the data acquisition system according to the current invention. Similarly, "sparse-channel projection data" is projection data based upon the sparse channel data.

After projection data is acquired using the above described sparse channel embodiments according to the current invention, the sparse channel data is processed using chord based reconstruction methods, which performs a differentiation of the data and then backprojection. The chord based reconstruction methods subsequently performs a Hilbert transform. In one example, by further algebraic manipulation, the differentiation is optionally restricted to the segment and view directions without the channel direction along which data is sparsely sampled. In the same example, the channel density is traded for view density.

Figure 2A:
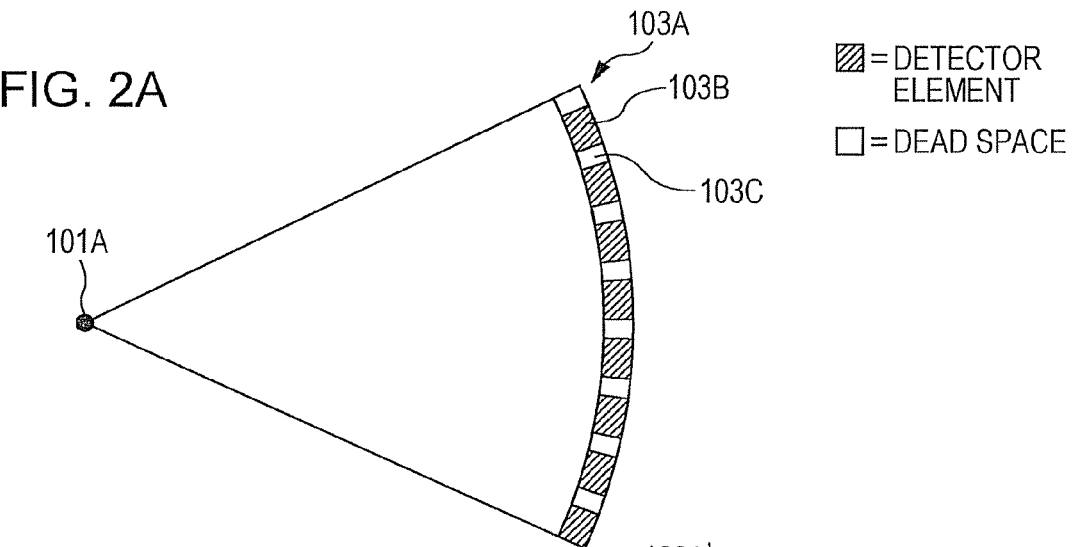
FIG. 2A is a diagram illustrating a portion of a prior art configuration having a full complement of detector cells or detector elements the third-generation geometry.
Figure 2B:
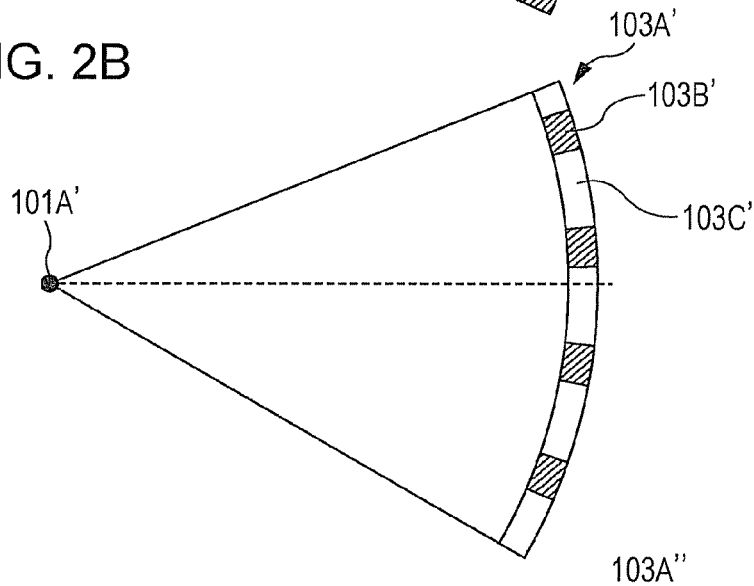
FIG. 2B is a diagram illustrating a portion of one embodiment of a sparse-channel X-ray detector having a less-than full complement of detector cells or detector elements in the third generation geometry.
Figure 2C:
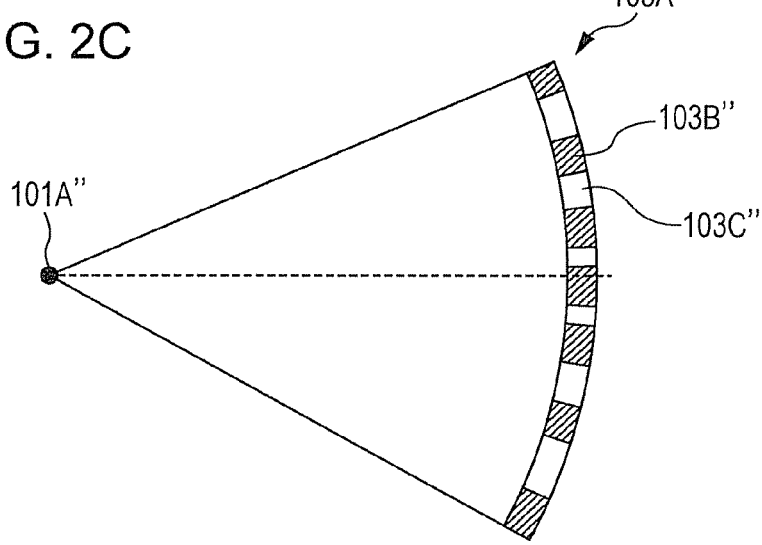
FIG. 2C is a diagram illustrating a portion of another embodiment of a sparse-channel X-ray detector having a less-than full complement of detector cells.

Now referring to FIGS. 2A, 2B and 2C, diagrams illustrate a comparison among detector cell configurations in one dimension according to the current invention and the prior art. With respect to the diagrams, an effective area or space of a detector cell is an area where a single detector cell occupies while a dead area or space is an area where no detector cell occupies. For the purpose of this application, the effective area or space is considered substantially the same as the physical size of a detector cell, which is indicated by a dark box.

FIG. 2A is a diagram illustrating a portion of a prior art configuration having a full complement of detector cells or detector elements the third-generation geometry. An X-ray source 101A is located opposite an X-ray detector 103A across a region of interest to be imaged by X rays. In the prior art configuration, the detector cells 103B are indicated by a row of equal-size dark boxes along one channel direction or one dimension. Between the detector cells 103B, dead spaces 103C are indicated by a row of light boxes also along the same channel direction or one dimension. The dead spaces 103C are empty spaces that are not occupied by the detector cells 103B. A pitch is defined to be a distance between two centers of the adjacent detector cells 103B.

FIG. 2B is a diagram illustrating a portion of one embodiment of a sparse-channel X-ray detector 103A' having a less-than full complement of detector cells or detector elements 103B' in the third generation geometry. An X-ray source 101A' is located opposite the X-ray detector 103A' across a region of interest to be imaged by X rays. In an exemplary embodiment, the detector cells 103B' are indicated by a row of equal-size dark boxes along one channel direction or one dimension. Between the detector cells 103B', dead spaces 103C' are indicated by a row of light boxes also along the same channel direction or one dimension. The dead spaces 103C' are empty spaces that are not occupied by the detector cells 103B'. A pitch is defined to be a distance between two centers of the adjacent detector cells 103B'. The pitch of every pair of the detector cells 103B' is larger than that of the detector cells 103B of the prior art detector 103A in FIG. 2A.

Still referring to FIG. 2B, the detector cells 103B' are placed at a predetermined equidistance with each other. In other words, the increased pitch is the same between any pair of the adjacent detector cells 103B' across the X-ray detector 103A'. The diagram may be considered as a cross sectional view of the X-ray detector 103A'. The diagram also may be considered to indicate a fan beam that is emitted from the X-ray source 101A'. Alternatively, the diagram illustrates a one-dimensional array detector 103A'.

Lastly, the detector cells 103B' are asymmetrical about the dotted central line in one embodiment of the X-ray detector 103A' according to the current invention. The detector cells 103B' are shifted or rotated by one quarter pixel or a predetermined angle in a counter-clock direction. The quarter-offset design is known in the CT scanners in order to promote the fill-in effect so as to improve the sampling density level while the X-ray detector 103A' rotates.

FIG. 2C is a diagram illustrating a portion of another embodiment of a sparse-channel X-ray detector 103A" having a less-than full complement of detector cells 103B". An X-ray source 101A" is located opposite the X-ray detector 103A" across a region of interest to be imaged by X rays. In an exemplary embodiment, the detector cells 103B" are indicated by a row of equal-size dark boxes along one channel direction or one dimension. Between the detector cells 103B", dead spaces 103C" are indicated by a row of light boxes also along the same channel direction or one dimension. The dead spaces 103C" are empty spaces that are not occupied by the detector cells 103B". A pitch is defined to be a distance between two centers of the adjacent detector cells 103B". The pitch of at least some of the detector cells 103B" is larger than that of the detector cells 103B of the prior art detector 103A in FIG. 2A.

Still referring to FIG. 2C, the detector cells 103B" are placed at a predetermined distance with each other. In other words, the increased pitch is not necessarily the same among pairs of the adjacent detector cells 103B" across the X-ray detector 103A'. In the illustrated embodiment, the pitch increases from the central region toward the peripheral region. In alternative embodiment, the pitch in peripheral regions is larger than that in central regions without gradual increase. The diagram may be considered as a cross sectional view of the X-ray detector 103A". The diagram also may be considered to indicate a fan beam that is emitted from the X-ray source 101A". Alternatively, the diagram illustrates a one-dimensional array detector 103A".

Lastly, the detector cells 103B" are asymmetrical about the dotted central line in one embodiment of the X-ray detector 103A" according to the current invention. The detector cells 103B" are shifted or rotated by one quarter pixel or a predetermined angle in a counter-clock direction. The quarter-offset design is known in the CT scanners in order to promote the fill-in effect so as to improve the sampling density level while the X-ray detector 103A" rotates.

Figure 3:
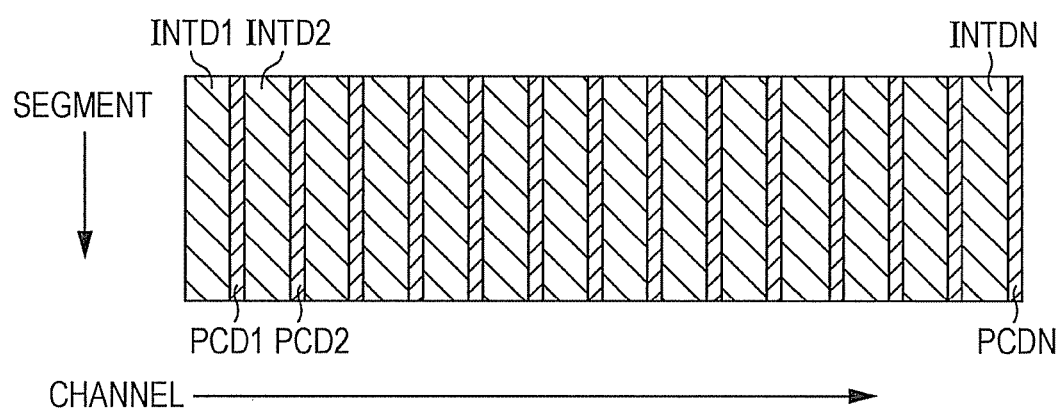
FIG. 3 is a diagram illustrating one embodiment of a basic hybrid detector to be utilized in the CT scanner system according to the current invention.

Now referring to FIG. 3, a diagram illustrates one embodiment of a basic hybrid detector in the CT scanner system according to the current invention. In one embodiment of the hybrid detector, the detector array 103A-1 includes a plurality of photon counting detectors (PCD) and integrating detectors (INTD) in a predetermined alternating pattern. The detector elements are placed in the segment direction and the channel direction as respectively indicated by the arrows near the detector array 103A-1. Along the channel direction, the photon counting detector (PCD) units or the photon counting detectors (PCD) are sparsely and equidistantly placed at the fixed positions in one embodiment according to the current invention. In the illustrated embodiment, the integrating detector (INTD) units or the integrating detectors (INTD) are placed between the two adjacent ones of the photon counting detector (PCD) units except one on the first integrating detector unit INTD1. Each of the photon counting detector (PCD) units consists of N×1 PCD detector elements while each of the integrating detector (INTD) units consists of N×M such as 64×24 integrating detector elements. Because of the above difference in the channel size, the photon counting detectors (PCD) are sparsely located in the channel direction with respect to the integrating detectors (INTD).

Still referring to FIG. 3, the hybrid detector is used in the detector unit in the third-generation geometry and or the fourth-generation geometry. The detector array 103A-1 forms an arc whose middle portion is centered at a predetermined x-ray source in a third generation CT geometry. The detector array 103A-1 is mounted on the surface of the detector unit 103 in one embodiment. The detector array 103A-1 also optionally forms a cylinder whose center is configured at the iso-center in the fourth generation CT geometry. In another embodiment, the PCDs and INTDs are optionally placed on different surfaces such as tunnel or grid for substantially reducing scatter during sampling. Other embodiments of the hybrid detector are not limited to the illustrated pattern or the above specified row/column configurations. One alternative embodiment includes only sparsely positioned photon counting detectors (PCD) at the predetermined equidistant positions without the integrating detectors (INTD).

Figure 4:
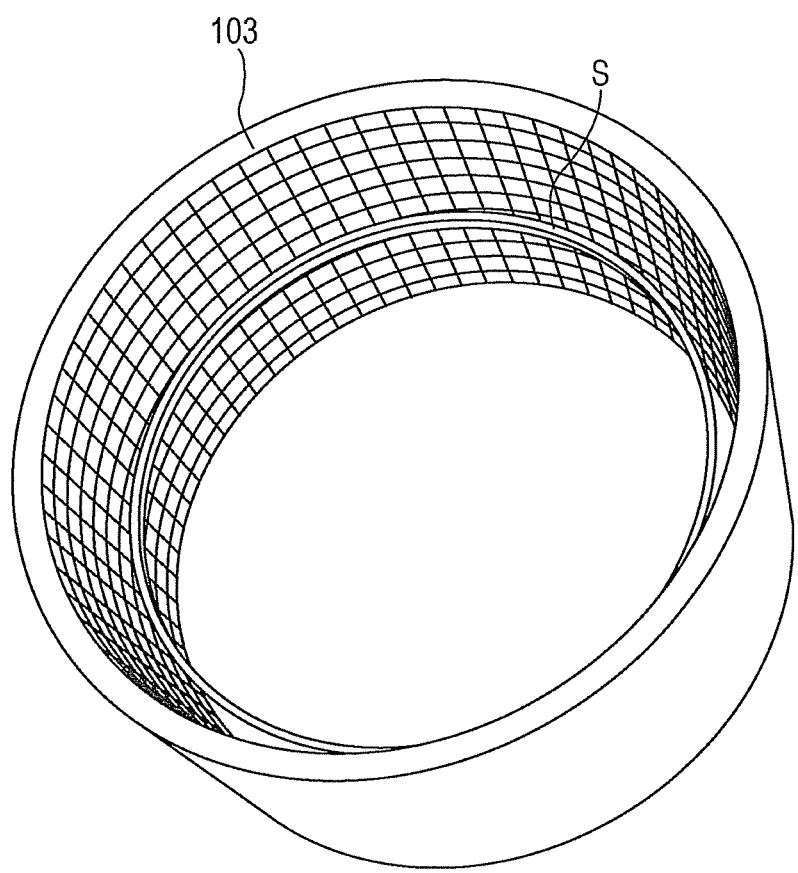
FIG. 4 is a diagram illustrating a fourth-generation detector geometry.

Now referring to FIG. 4, a diagram illustrates a fourth-generation detector geometry. A cylindrical detector 103 has internal surfaces where multiple row of detectors are mounted. A circle S indicates the source trajectory. The detector pitch in channel (fan) direction is substantially larger than the detector pitch in segment (cone) direction while sampling over the source trajectory is substantially dense. In a conventional analytical reconstruction, a filtering in the channel direction is performed, and the filtered result leads to a substantially large error in the filtered data due to the large pitch. Consequently, this error degrades the spatial resolution and causes blurring in the final images.

Figure 5:
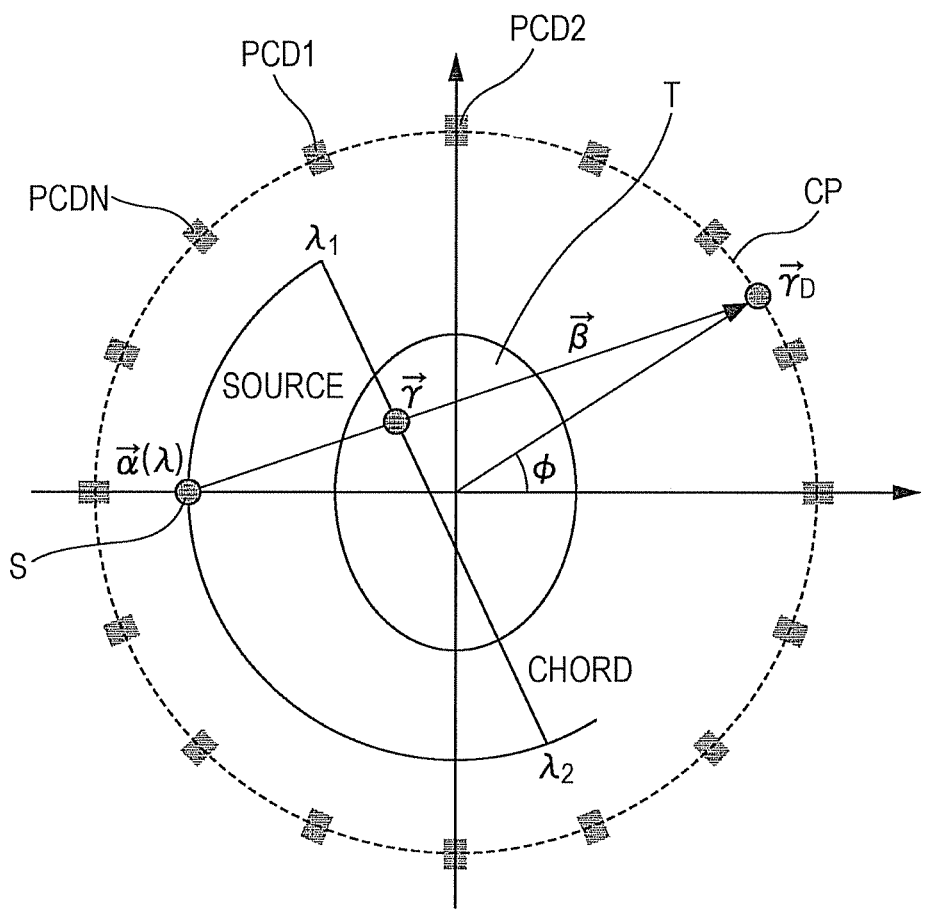
FIG. 5 is a diagram illustrating a problem associated with a sparse detector in the channel direction.

Now referring to FIG. 5, a diagram illustrates a problem associated with a sparse detector in the channel direction. In one embodiment of the sparse detector, the photon counting detector elements PCD1 through PCDN are sparsely positioned around an object OBJ in the fourth-generation geometry along a predetermined circular path CP at predetermined fixed and equidistant positions, and the sparsity is along the channel direction. Furthermore, an X-ray source S rotates inside the fourth-generation detector around the object OBJ in the embodiment. After the data is sampled through the above described sparse detector elements along the channel direction, the acquired data is differentiated along the channel, segment and view directions. Due to the sparsity in the channel direction, the differentiation along the channel direction contributes a substantial error in reconstructing an image. Consequently, the reconstructed images are blurred and or contain artifacts. The third-generation detector with a similar sparsity is optionally utilized, and the substantially identical problem results in the reconstructed images.

In two-dimensional (2D) reconstruction for 4th generation CT with the sparse detectors PCD1 through PCDN, the fan beam data with a vertex at the source S can be transformed into fan beam data with a vertex at detectors through rebinning. Since the sampling along the source trajectory is dense, the sampling of the transformed data is still dense in the fan direction but sparse in the view direction. An analytical fan beam reconstruction performs filtering in the fan direction and results in reasonable image quality for moderate sparse view sampling. On the other hand, without the transform, the image is blurring due to the sparse sampling in the fan direction.

In three-dimensional (3D) reconstruction for 4th generation CT with the sparse detectors PCD1 through PCDN, the existing analytical reconstruction algorithms filter or differentiate the sampled data. For example, an X-ray source travels a predetermined helical trajectory while data is sampled at dense detector elements in the segment direction as well as at sparse detector elements in the channel direction. The existing analytical reconstruction algorithms either filter or differentiate the above sampled data along the channel direction. Ultimately, an image is reconstructed based upon the differentiated data. Due to the sparsely positioned detector elements along the channel direction, the reconstructed image is substantially blurred depending upon a degree of the sparsity. Although the 2D approximation is optionally used, cone beam artifacts may be still problematic.

Still referring to FIG. 5, the differentiated data is defined in terms of parameters in the diagram, and the equations depict backprojection of the differentiated data. In general, an arbitrary image is considered on a chord for the purpose of the chord based reconstruction method according to the current invention as expressed by Equation (0) below. The parameters will be described with respect to FIG. 6 below.

$$f(x_c, \lambda_1, \lambda_2) = \frac{1}{2\pi^2} \int \frac{d\bar{x}_c}{x_c - \bar{x}_c} f_H(\bar{x}_c, \lambda_1, \lambda_2) \qquad (0)$$

Equation (1) define a backprojection function for the differentiated data in the chord-based reconstruction.

$$f_H(x_c, \lambda_1, \lambda_2) = \int_{\lambda_1}^{\lambda_2} \frac{d\lambda}{|\vec{r} - \vec{a}(\lambda)|} \left[ \frac{\partial g(\lambda, \varphi, v)}{\partial \lambda} \right]_{\vec{\beta}} \qquad (1)$$

Equation (2) below defines the differentiated data.

$$\left[ \frac{\partial g(\lambda, \varphi, v)}{\partial \lambda} \right]_{\vec{\beta}} = \frac{\partial g(\lambda, \varphi, v)}{\partial \lambda} + \frac{\partial g(\lambda, \varphi, v)}{\partial \varphi} \left[ \frac{\partial \varphi}{\partial \lambda} \right]_{\vec{\beta}} + \frac{\partial g(\lambda, \varphi, v)}{\partial v} \left[ \frac{\partial v}{\partial \lambda} \right]_{\vec{\beta}} \qquad (2)$$

where $g(\lambda, \varphi, v)$ is projection data at a view index or view angle $\lambda$, a channel index or channel angle $\varphi$, and a segment index or cone angle $v$.

Figure 6:
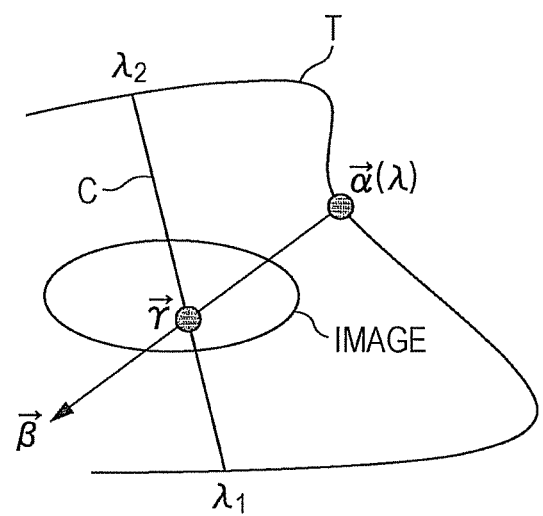
FIG. 6 is a diagram illustrating the relationship between an image and a chord as used in one process of reducing undesirable features in a reconstructed image based upon the sampled data at the detector having sparsity at least in on direction according to the current invention.

Now referring to FIG. 6, a diagram illustrates the relationship between an image and a chord as used in one process of reducing undesirable features in a reconstructed image based upon the sampled data at the detector having sparsity at least in on direction according to the current invention. In general, the chord is a part of the chord-line that is a straight line intersecting with the source trajectory at two points. Thus, a chord C is defined as a line intersecting a trajectory T at a pair of points $\lambda_1, \lambda_2$, a point on the chord C is designated by a spatial vector $\vec{r}$. The projection direction $\vec{\beta}$ of an individual x-ray is defined as in Equation (3) when the source is at the trajectory position $\vec{a}(\lambda)$ and passes through the chord point $\vec{r}$.

$$\vec{\beta} = \frac{\vec{r} - \vec{a}(\lambda)}{|\vec{r} - \vec{a}(\lambda)|} \qquad (3)$$

In one exemplary process of substantially reducing the undesirable effects of the sample data in reconstructing an image according to the current invention, the differentiation is eliminated in a direction that is most sparsely sampled. For example, assuming that the data is sampled most sparsely along the channel direction, the term $$\frac{\partial g(\lambda, \varphi, v)}{\partial \varphi} \left[ \frac{\partial \varphi}{\partial \lambda} \right]_{\vec{\beta}}$$

is eliminated from Equation (2) in one exemplary process according to the current invention. The angle $\varphi$ is a channel angle as indicated in the diagram of FIG. 5.

Furthermore, in one exemplary process of substantially reducing the undesirable effects of the sampled data in reconstructing an image according to the current invention, proper weights are determined to compensate for the data that is sparsely sampled along at least one direction. In one example, after the differentiation of the sample data is eliminated along the channel direction, a proper weight A is determined as defined in Equation (4).

$$A(x_c, \lambda, \varphi, v) = \left[ \frac{\partial \varphi}{\partial \lambda} \right]_{\vec{\beta}} \left[ \frac{\partial \lambda}{\partial \varphi} \right]_r \qquad (4)$$

where the weight A depends upon an image point $x_c$, view $\lambda$, channel $\varphi$, and segment $v$. By the same token, a proper weight B is determined as defined in Equation (5).

$$B(x_c, \lambda, \varphi, v) = \left[ \frac{\partial \varphi}{\partial \lambda} \right]_{\vec{\beta}} - \left[ \frac{\partial v}{\partial \lambda} \right]_r \left[ \frac{\partial \varphi}{\partial \lambda} \right]_{\vec{\beta}} - \left[ \frac{\partial v}{\partial \lambda} \right]_r \qquad (5)$$

Where $$\left( \frac{\partial \varphi}{\partial \lambda} \right)_{\vec{\beta}} = \frac{\beta_x \dot{a}_y(\lambda) - \beta_y \dot{a}_x(\lambda)}{R_D(\beta_x \cos\varphi + \beta_y \sin\varphi)}$$

$$\left( \frac{\partial v}{\partial \lambda} \right)_{\vec{\beta}} = -\beta_z \frac{\dot{a}_x(\lambda) \cos\varphi - \dot{a}_y(\lambda) \sin\varphi}{\beta_x \cos\varphi + \beta_y \sin\varphi}$$

$$\left( \frac{\partial \varphi}{\partial \lambda} \right)_r = \frac{\beta_x \dot{a}_y(\lambda) - \beta_y \dot{a}_x(\lambda) + \beta_x t_D \left( \frac{(\vec{a}(\lambda) \cdot \vec{\beta})\beta_y - \dot{a}_y(\lambda)}{|\vec{r} - \vec{a}(\lambda)|} \right) - \beta_y t_D \left( \frac{(\vec{a}(\lambda) \cdot \vec{\beta})\beta_x - \dot{a}_x(\lambda)}{|\vec{r} - \vec{a}(\lambda)|} \right)}{R_D(\beta_x \cos\varphi + \beta_y \sin\varphi)}$$

$$\left( \frac{\partial v}{\partial \lambda} \right)_r =$$

$$-\beta_z \frac{\dot{a}_x(\lambda)\cos\varphi + \dot{a}_y(\lambda)\sin\varphi + t_D \sin\varphi \left( \frac{(\vec{a}(\lambda)\cdot\vec{\beta})\beta_y - \dot{a}_y(\lambda)}{|\vec{r}-\vec{a}(\lambda)|} \right) + t_D \cos\varphi \left( \frac{(\vec{a}(\lambda)\cdot\vec{\beta})\beta_x - \dot{a}_x(\lambda)}{|\vec{r}-\vec{a}(\lambda)|} \right)}{\beta_x \cos\varphi + \beta_y \sin\varphi} +$$

$$t_D \left( \frac{(\vec{a}(\lambda)\cdot\vec{\beta})\beta_z - \dot{a}_z(\lambda)}{|\vec{r}-\vec{a}(\lambda)|} \right)$$

The above defined proper weights A and B of Equations (4) and (5) are applied with respect to Equation (1) above. Consequently, Equation (6) below is obtained.

$$f_H(x_c, \lambda_1, \lambda_2) = \qquad (6)$$
$$\int_{\lambda_1}^{\lambda_2} \frac{d\lambda}{|\vec{r}-\vec{a}(\lambda)|} \left\{ A(x_c, \lambda, \varphi, v) \left[ \frac{\partial g(\lambda, \varphi, v)}{\partial \lambda} \right]_{\vec{r}} + (1 - A(x_c, \lambda, \varphi, v)) \frac{\partial g(\lambda, \varphi, v)}{\partial \lambda} + B(x_c, \lambda, \varphi, v) \frac{\partial g(\lambda, \varphi, v)}{\partial \lambda} \right\}$$

Ultimately, Equation (6) is also expressed by Equation (7).

$$f_H(x_c, \lambda_1, \lambda_2) = \frac{A(x_c, \lambda, \varphi, v) g(\lambda, \varphi, v)}{|\vec{r}-\vec{a}(\lambda)|} \bigg|_{\lambda_1}^{\lambda_2} - \qquad (7)$$
$$\int_{\lambda_2}^{\lambda_1} d\varphi \left[ \frac{\partial \lambda}{\partial \varphi} \right]_r g(\lambda, \varphi, v) \frac{\partial}{\partial \lambda} \left( \frac{A(x_c, \lambda, \varphi, v)_r}{|\vec{r}-\vec{a}(\lambda)|} \right)_r + \int_{\lambda_2}^{\lambda_1} \frac{d\varphi}{|\vec{r}-\vec{a}(\lambda)|} \left[ \frac{\partial \lambda}{\partial \varphi} \right]_r$$
$$\left\{ (1 - A(x_c, \lambda, \varphi, v)) \frac{\partial g(\lambda, \varphi, v)}{\partial \lambda} + B(x_c, \lambda, \varphi, v) \frac{\partial g(\lambda, \varphi, v)}{\partial v} \right\}$$

Figure 7:
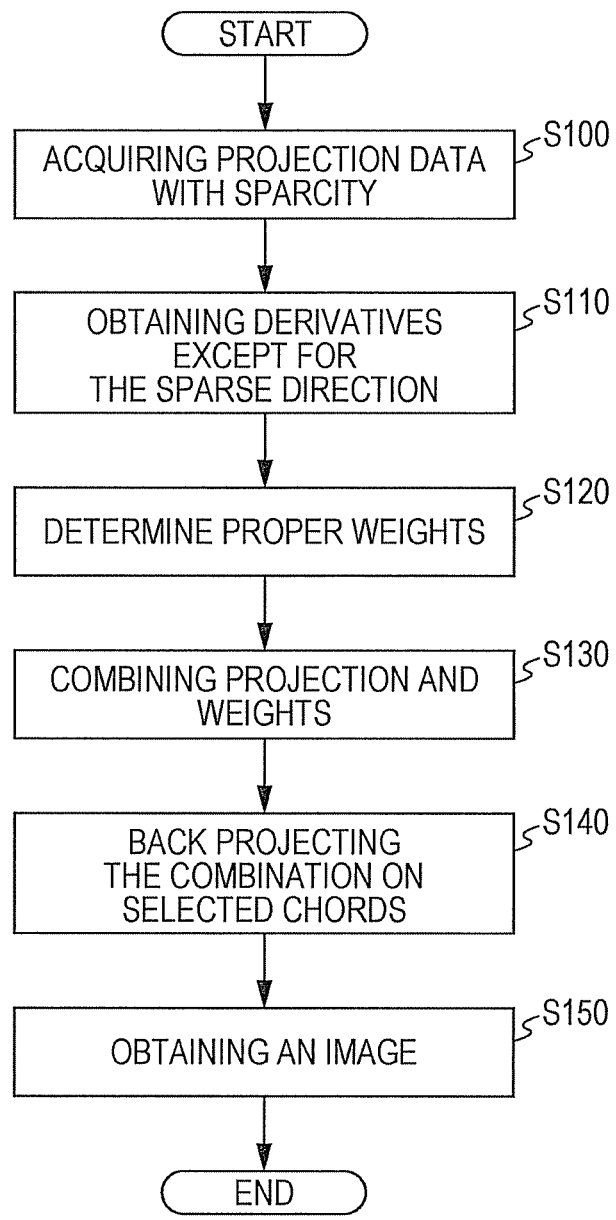
FIG. 7 is a flow chart illustrating steps or acts involved in a process of substantially reducing undesirable effects of the sample data having sparsity along one direction of the detector in reconstructing an image according to the current invention.

Now referring to FIG. 7, a flow chart illustrates steps or acts involved in a process of substantially reducing undesirable effects of the sample data having sparsity along one direction of the detector in reconstructing an image according to the current invention. That is, one exemplary process of the reconstruction algorithm in Cone Beam CT substantially reduces blurring in reconstructing an image based upon sample data having differentiation in one direction on the detector according to the current invention. In one particular example, the data has been acquired with sparse detector cells or elements in the channel direction. Although certain aspects of the following steps or acts are described based upon the above exemplary data acquisition, the process of reducing the undesirable effects according to the current invention is not necessarily limited to the sampled data having sparsity in the channel direction on the detector.

In a step S100, projection data is acquired with a predetermined or known sparsity in a certain direction on the detector. In one exemplary process, projection data is acquired with a two-dimensional (2D) detector array whose detector elements are sparse in the channel direction with a circular or helical source trajectory. In a particular implementation, the above 2D detector array is configured in the fourth-generation geometry to form a fixed cylinder, and an X-ray source travels over a circular or helical path inside the cylindrical detector.

In a step S110, the acquired projection data is now processed by differentiating along certain selected directions with respect to the detector and the source trajectory according to the current invention. In the above described exemplary process, the sparsity exists in the channel direction. Alternatively, the channel direction is the most sparse in sampling among the segment, view and channel directions. Based upon the above sparsity condition in the acquired projection data, the derivatives are obtained only along the segment and view directions and the derivative along the channel direction is eliminated. That is, the second term of the right hand side of Equation (2) is not determined.

In a step S120, predetermined proper weights are determined in view of the above sparsity condition in the acquired projection data according to the current invention. In an exemplary process, a pair of the proper weights A and B is respectively determined according to Equations (4) and (5) to compensate for the sparsity condition in the acquired projection data. The proper weights A and B are determined for the corresponding derivatives. Although the specific definitions are provided in to Equations (4) and (5), the proper weights are optionally fine tuned in other exemplary processes.

In a step S130, the projection data and the derivatives are combined with the proper weights according to the current invention. In an exemplary process, a pair of the proper weights A and B are applied in the combining the projection data and the derivatives as indicated in Equation (6). In other words, the proper weights are applied to the derivatives so as to obtain the weighted derivatives based upon the derivatives and the proper weights. Subsequently, the projection data and the weighted derivatives are combined to generate combination data.

In a step S140, a family of chords is selected according to the source trajectory and the combination data after the above step S130 is backprojected onto the selected chords in one exemplary process according to the current invention. As described above with respect to FIG. 6, the chord is a part of the chord-line that is a straight line intersecting with the source trajectory at two points. For example, a chord C in FIG. 6 is defined as a line intersecting a trajectory T at a pair of points $\lambda_1, \lambda_2$, a point on the chord C is designated by a spatial vector $\bar{r}$.

In a step S150, an image is obtained after the step S140. In one exemplary process according to the current invention, a finite Hilbert transform is performed on the selected chords to obtain images on the chords. Finally, the images on the chords are transformed onto the Cartesian coordinates.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of reconstructing an image in cone beam CT, comprising:
    acquiring projection data at a detector while scanning an object in a predetermined manner;
    selecting one of a predetermined set of directions, the selected direction being the least sampled direction;
    obtaining derivatives along the directions in the projections data except for the selected direction;
    determining proper weights corresponding to the derivatives;
    obtaining weighted derivatives based upon the derivatives and the proper weights;
    combining the projection data and the weighted derivatives to generate combination data; and
    backprojecting the combination data.

2. The method of reconstructing an image in cone beam CT according to claim 1 wherein the backprojecting step further comprising:
    selecting a family of chords according to a source trajectory;
    backprojecting the combination data onto the selected chords;
    obtaining images on the selected chords by performing Hilbert transform; and
    transforming the images on the chords onto the Cartesian coordinates.

3. The method of reconstructing an image in cone beam CT according to claim 1 wherein the directions include a channel direction, a segment direction and a view direction.

4. The method of reconstructing an image in cone beam CT according to claim 3 wherein the proper weights are determined based upon A and B when a derivative for a channel direction is eliminated:

$$A(x_c, \lambda, \varphi, v) = \left[\frac{\partial v}{\partial \lambda}\right]_{\bar{\beta}} \left[\frac{\partial \lambda}{\partial \varphi}\right]_r$$

$$B(x_c, \lambda, \varphi, v) = \left[\frac{\partial v}{\partial \lambda}\right]_{\bar{\beta}} - \left[\frac{\partial v}{\partial \lambda}\right]_r \left[\frac{\partial \varphi}{\partial \lambda}\right]_{\bar{\beta}} \left[\frac{\partial \lambda}{\partial \varphi}\right]_r.$$

5. The method of reconstructing an image in cone beam CT according to claim 1 wherein the projection data is acquired at the detector in the fourth-generation geometry.

6. The method of reconstructing an image in cone beam CT according to claim 1 wherein the projection data is acquired at the detector in the third-generation geometry.

7. The method of reconstructing an image in cone beam CT according to claim 1 wherein the projection data is acquired at the detector having sparsely placed detector elements in a predetermined channel direction.

8. A system for reconstructing an image in cone beam CT, comprising:
- a data acquisition unit for acquiring projection data at a detector while scanning an object in a predetermined manner; and
- a reconstruction device connected to said data acquisition unit for selecting one of a predetermined set of directions, the selected direction being the least sampled direction, said reconstruction device obtaining derivatives along the directions in the projections data except for the selected direction, said reconstruction device determining proper weights corresponding to the derivatives, said reconstruction device obtaining weighted derivatives based upon the derivatives and the proper weights, said reconstruction device combining the projection data and the weighted derivatives to generate combination data, said reconstruction device backprojecting the combination data.

9. The system for reconstructing an image in cone beam CT according to claim 8 wherein said reconstruction device further performing the tasks of:
- selecting a family of chords according to a source trajectory;
- backprojecting the combination data onto the selected chords;
- obtaining images on the selected chords by performing Hilbert transform; and
- transforming the images on the chords onto the Cartesian coordinates.

10. The system for reconstructing an image in cone beam CT according to claim 8 wherein the directions include a channel direction, a segment direction and a view direction.

11. The system for reconstructing an image in cone beam CT according to claim 10 wherein said reconstruction device determines the proper weights based upon A and B when a derivative for a channel direction is eliminated:

$$A(x_c, \lambda, \varphi, v) = \left[\frac{\partial \varphi}{\partial \lambda}\right]_{\vec{\beta}} \left[\frac{\partial \lambda}{\partial \varphi}\right]_r$$

$$B(x_c, \lambda, \varphi, v) = \left[\frac{\partial v}{\partial \lambda}\right]_{\vec{\beta}} - \left[\frac{\partial v}{\partial \lambda}\right]_r \left[\frac{\partial \varphi}{\partial \lambda}\right]_{\vec{\beta}} \left[\frac{\partial \lambda}{\partial \varphi}\right]_r.$$

12. The system for reconstructing an image in cone beam CT according to claim 8 wherein the detector is in the fourth-generation geometry.

13. The system for reconstructing an image in cone beam CT according to claim 8 wherein the detector in the third-generation geometry.

14. The system for reconstructing an image in cone beam CT according to claim 8 wherein the detector has sparsely placed detector elements in a predetermined channel direction.

* * * * *